(12) United States Patent
LaVon et al.

(10) Patent No.: US 9,039,669 B1
(45) Date of Patent: May 26, 2015

(54) DISPOSABLE PULL-ON GARMENT

(71) Applicant: The Procter & Gamble Company, Cincinnati, OH (US)

(72) Inventors: Gary Dean LaVon, Liberty Township, OH (US); Masaharu Nishikawa, Cincinnati, OH (US); Jacob Alan Barnhorst, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/249,985

(22) Filed: Apr. 10, 2014

Related U.S. Application Data

(63) Continuation of application No. 13/764,990, filed on Feb. 12, 2013.

(60) Provisional application No. 61/598,012, filed on Feb. 13, 2012.

(51) Int. Cl.
*A61F 13/15* (2006.01)
*A61F 13/49* (2006.01)

(52) U.S. Cl.
CPC . *A61F 13/49011* (2013.01); *A61F 2013/49041* (2013.01)

(58) Field of Classification Search
CPC ........... A61F 5/44; A61F 13/15; A61F 13/47; A61F 13/49; A61F 13/51; A61F 13/514; A61F 13/537; A61F 13/56; A61F 13/62
See application file for complete search history.

(56) References Cited

U.S. PATENT DOCUMENTS

| | | | |
|---|---|---|---|
| 5,735,839 A | 4/1998 | Kawaguchi et al. | |
| 5,749,865 A | 5/1998 | Yamamoto et al. | |
| 5,916,206 A | 6/1999 | Otsubo et al. | |
| 5,941,865 A | 8/1999 | Otsubo et al. | |
| 6,726,669 B2 | 4/2004 | Shimada et al. | |
| 2007/0287975 A1 | 12/2007 | Fujimoto et al. | |
| 2011/0004175 A1* | 1/2011 | Veith | 604/367 |
| 2013/0310796 A1* | 11/2013 | Zink et al. | 604/392 |

OTHER PUBLICATIONS

PCT Search Report dated May 13, 2013, 10 pages.
U.S. Appl. No. 13/764,990, filed Feb. 11, 2013: Preinterview First Office Action, mail date Sep. 11, 2014, 15 pages.
U.S. Appl. No. 14/250,043, filed Apr. 10, 2014: Non-Final Rejection, mail date Jul. 28, 2014, 18 pages.

\* cited by examiner

*Primary Examiner* — Melanie Hand
(74) *Attorney, Agent, or Firm* — Andres E. Velarde

(57) ABSTRACT

An absorbent article having a longitudinal centerline, a front region, a crotch region, and a back region. The absorbent article has a main portion, a side portion, and a waist portion. The waist portion has a belt portion that has a front belt portion having elastomeric material and a back belt portion having elastomeric material. The front belt portion has a first elastic section and a second elastic section, each section having force zones. The back belt portion has a third elastic section and a fourth elastic section, each section having force zones. The force zones in the portions alternate between a high force zone and a low force zone in at least one belt portion.

12 Claims, 11 Drawing Sheets

DISPOSABLE PULL-ON GARMENT

FIELD OF THE INVENTION

The present invention relates to disposable pull-on garments.

BACKGROUND OF THE INVENTION

Infants and other incontinent individuals wear disposable absorbent articles such as diapers to receive and contain urine and other body exudates. Training pants or pull-on diapers have become popular for use on children able to walk and often who are toilet training. Many disposable pull-on garments use elastic elements secured in an elastically contractible condition in the waist and/or leg openings. Typically, in order to insure full elastic fit about the leg and the waist such as is provided with durable undergarments, the leg openings and waist opening are encircled at least in part with elasticized bands of rubber or other materials positioned along the periphery of the respective opening.

While it may be believed that a stretchable waist opening generating high contraction force contributes to anchoring the waist opening of the pull-on diapers to the wearer's body, such high contraction force sometimes causes not only difficulty for a caregiver to apply and remove the absorbent article, but may also cause sagging of the waist opening of the pull-on diaper. The front portion of the waist opening is positioned on stomach of the wearer, which is considered a high motion zone that undergoes repeated expansion and contraction as the wearer breathes, sits, squats or bends. When the stomach expands, the contraction force increases to generate a relatively higher anchoring force. However, as the contraction force increases, the component force of the contraction wants to move from the high force state to a lower force state and as such the elasticized region tends to move from the higher circumference higher force region toward the crotch along the curvature of the belly to a smaller circumference lower force region of the wearer. In other words, when a relatively high component force is exerted on the stomach of the wearer especially wearers with a round belly, one wherein the waist circumference decreases toward the crotch of the wearer, the waist portion of the pull-on diaper will seek a minimum force state, i.e. smaller circumference thereby causing the diaper waist to sag.

In order to reduce potential sagging caused by high contraction force exerted on the stomach, high motion zone, it is conceivable to remove or reduce the elastic material in the front center waist portion and the back center waist portion. However, if the elastic material is removed therefrom, another drawback occurs. Namely, the front center waist portion has no contraction force and therefore may not adequately compensate for the movements of wearer. As a result, the front waist portion may flip over or may form gaps as a result of the wearer's movement. Such flipping-over or gapping of the waist portion is also as problematic as sagging since it gives a poor impression of the pull-on diaper to the wearer or caregiver and may result in a loss of performance, leakage of exudates from the article. Furthermore, improvements in the absorbent core have led to thinner more flexible absorbent structures that may also influence the way the elastic material interacts with the body thereby impacting the overall fit and performance of the product.

Based on the foregoing, there is a need for a disposable pull-on garment to provide an improved fit around the waist opening and/or leg openings. There is also a need for a disposable pull-on garment to improve sagging and or gapping problems around the waist opening. There is also a need for a disposable pull-on garment to improve flip-over problems in the waist portion. Additionally, there is a need for designing the waist opening to allow a caregiver to easily apply and remove the absorbent article.

SUMMARY OF THE INVENTION

An absorbent article having a longitudinal centerline, a front region, a crotch region, and a back region. The absorbent article has a main portion, a side portion, and a waist portion. The side portion is disposed transversely outboard of the main portion. The waist portion has a belt portion. The belt portion has a front belt portion having elastomeric material and a back belt portion having elastomeric material. The front belt portion has a first elastic section and a second elastic section. The first elastic section of the front belt portion has a first force zone, a second force zone, and a third force zone. The second elastic section of the front belt portion has a fourth force zone, fifth force zone, and a sixth force zone. The back belt portion has a third elastic section and a fourth elastic section. The third elastic section of the back belt has a seventh force zone, eighth force zone, and a ninth force zone. The fourth elastic section of the back belt comprises a tenth force zone, eleventh force zone, and a twelfth force zone. The individual force zones each comprise an individual force profile and the force profile of one or more of the second force zone, fifth force zone, eighth force zone and the eleventh force zone is greater than the force profile of their respective adjacent force zones.

An absorbent article having a longitudinal centerline, a front region, a crotch region, and a back region. The absorbent article has a main portion, a side portion, and a waist portion. The side portion is disposed transversely outboard of the main portion. The waist portion has a belt portion that has a front belt portion having elastomeric material and a back belt portion having elastomeric material. The front belt portion has a plurality of force zones. The back belt portion has a plurality of force zones. The plurality of force zones alternate between a high force zone and a low force zone in at least one belt portion.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). The pull-on garment is also preferably "absorbent" to absorb and contain the various exudates discharged from the body. A preferred embodiment of the absorbent article is the disposable absorbent pull-on garment, shown in FIG. 1.

As used herein, the term "absorbent article" refers to pull-on garments generally worn by infants and other incontinent individuals to absorb and contain urine, feces and/or menses. It should be understood, however, that the term absorbent article is also applicable to other garments such as training pants, incontinent briefs, feminine hygiene garments or panties, and the like.

As used herein, the terms "elastic," "elastomer," and "elastomeric" refer to a material which generally is able to extend to a strain of at least 50% without breaking or rupturing, and is able to recover substantially to its original dimensions, accounting for set, after the deforming force has been removed.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

Figure 1:
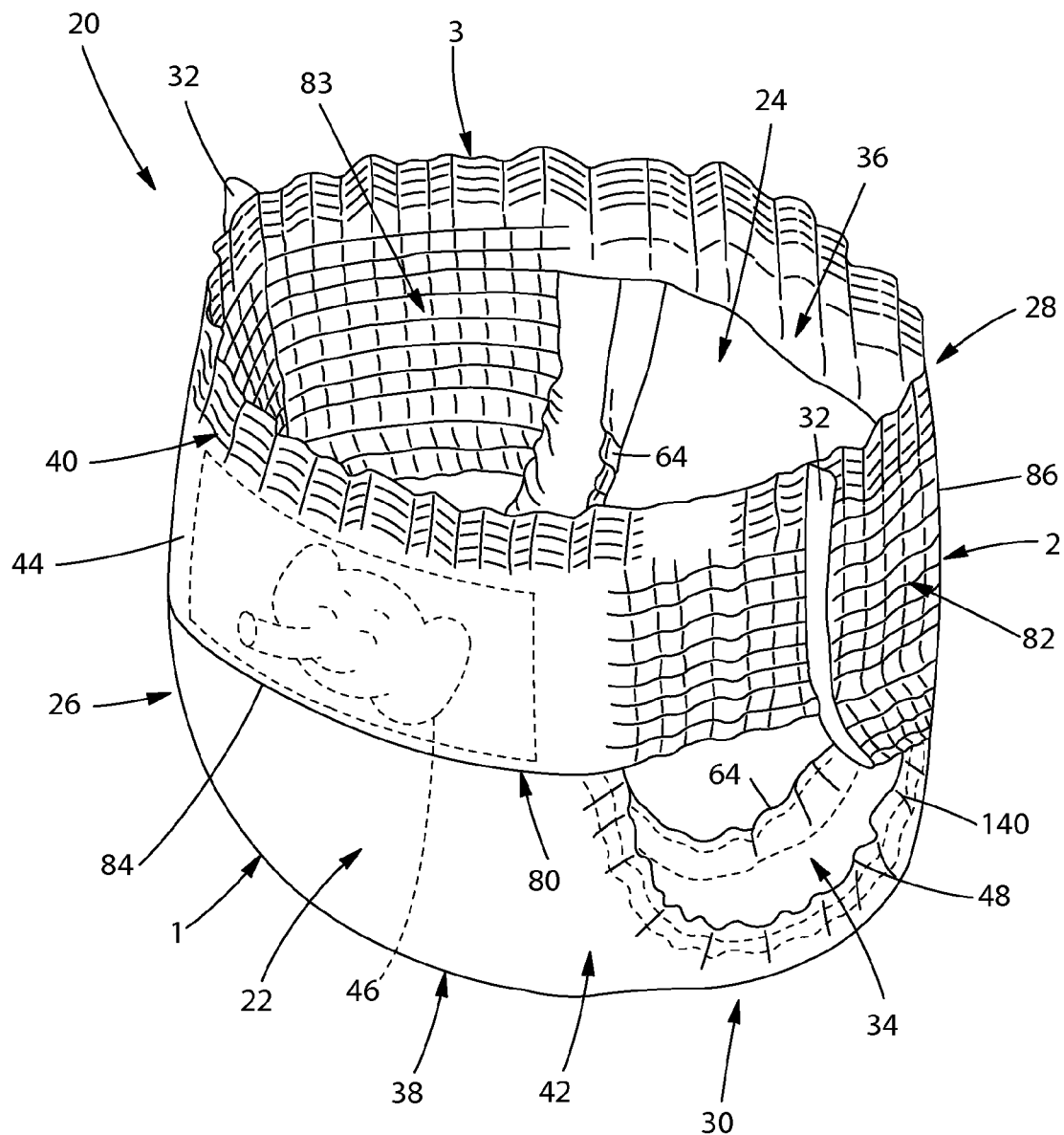
FIG. 1 is a perspective view of an exemplary disposable pull-on garment in a typical in-use configuration.
Figure 2:
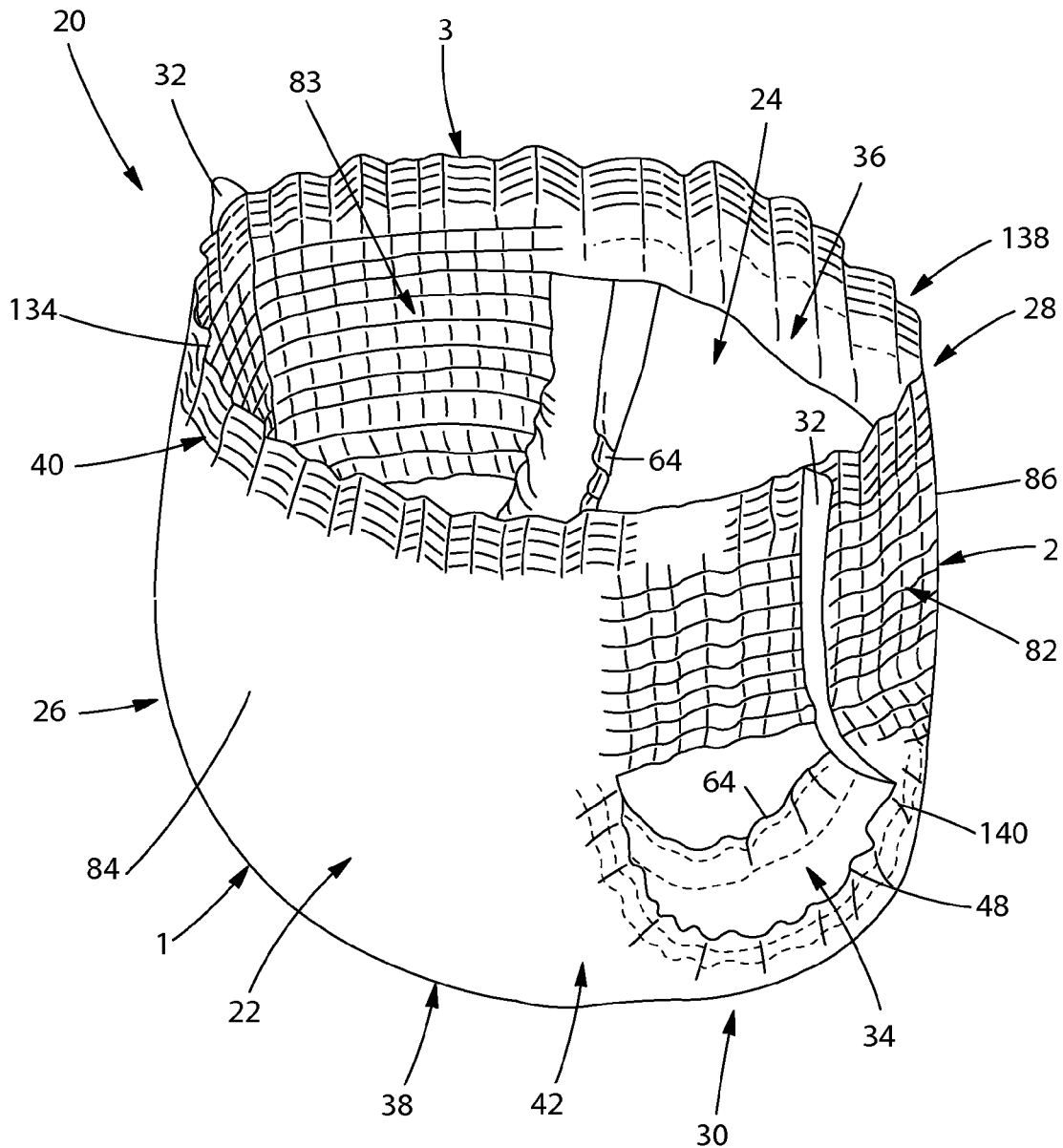
FIG. 2 is a perspective view of an exemplary disposable pull-on garment in a typical in-use configuration.

FIG. 1 is a perspective view of the absorbent article 20. FIG. 2 is a perspective view of the absorbent article 20. The absorbent article 20 has a longitudinal centerline L1 and a transverse centerline T1 (refer to FIG. 3 as well). The absorbent article 20 has an outer surface 22, an inner surface 24 opposed to the outer surface 22, a front region 26, a back region 28, a crotch region 30, and seams 32 which join the front region 26 and the back region 28 to form two leg openings 34 and a waist opening 36. Also referring to FIGS. 1-3, the absorbent article 20 comprises a main portion 1, a side portion 2, and a waist portion 3.

Figure 3:
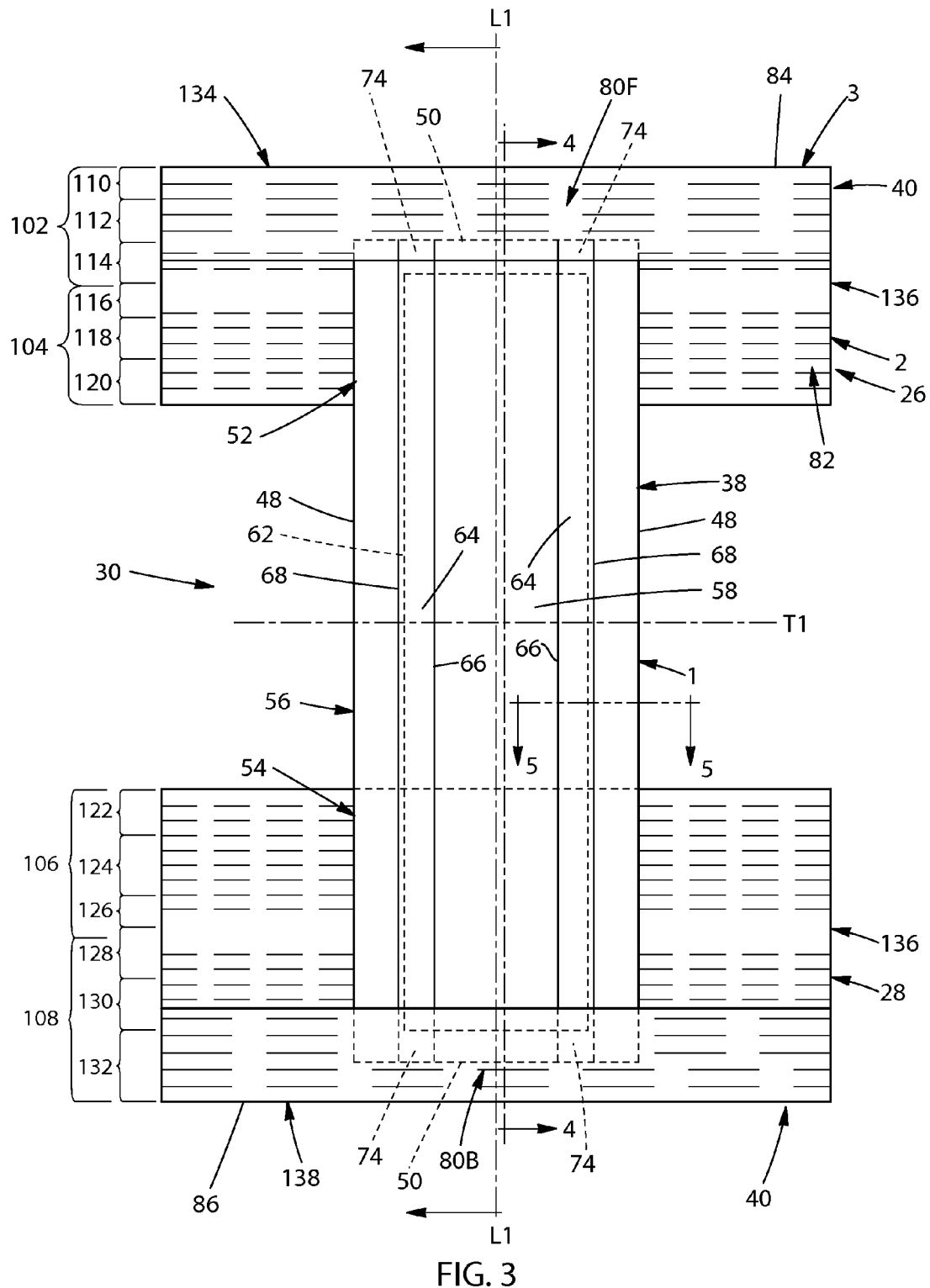
FIG. 3 is a plan view of the pull-on garment in its flat uncontracted condition showing the inner surface.

In the embodiment shown in FIGS. 1 and 3, the absorbent article 20 comprises an absorbent main body 38 (hereinafter may be referred to as "main body") to cover the crotch region of the wearer and a belt 40 extending transversely about the waist opening 36. The absorbent article 20 may also comprise an outer cover layer 42 to cover the main body 38. The belt 40 defines the waist opening 36. The belt 40, the main body 38 and/or the outer cover layer 42 jointly define the leg opening 34. The absorbent article 20 may have a patch sheet 44 printed with a graphic 46 thereon, which may be disposed in the front region 26 and/or the back region 28.

In the embodiment shown in FIG. 2 the absorbent article 20 comprises an absorbent main body 38 to cover the crotch region of the wearer and a belt 40 extending transversely about the waist opening 36. The absorbent article 20 may also comprise an outer cover layer 42 to cover the main body 38. The belt 40 defines the waist opening 36. The belt 40, the main body 38 and/or the outer cover layer 42 jointly define the leg opening 34. One or more of the belt layers may extend from a first waist edge 134 in a first waist region 26 through the crotch region to a longitudinally opposing second waist edge 138 in a second waist region 28 and may form a portion or the whole of the outer surface of the absorbent article 20.

The absorbent main body 38 absorbs and contains body exudates disposed on the main body 38. In the embodiment shown in FIG. 3, the main body 38 has a generally rectangular shape having a longitudinal centerline L1, a transverse centerline T1, left and right longitudinally extending side edges 48 (hereinafter may be referred to as "longitudinal side edge") and front and back transversely extending end edges 50 (hereinafter may be referred to as "transverse end edge"). The main body 38 also has waist panels (i.e., a front waist panel 52 positioned in the front waist region 26 of the absorbent article 20 and a back waist panel 54 positioned in the back waist region 28) and a crotch panel 56 in the crotch region 30 between the front and back waist panels 52, 54.

Figure 4A:
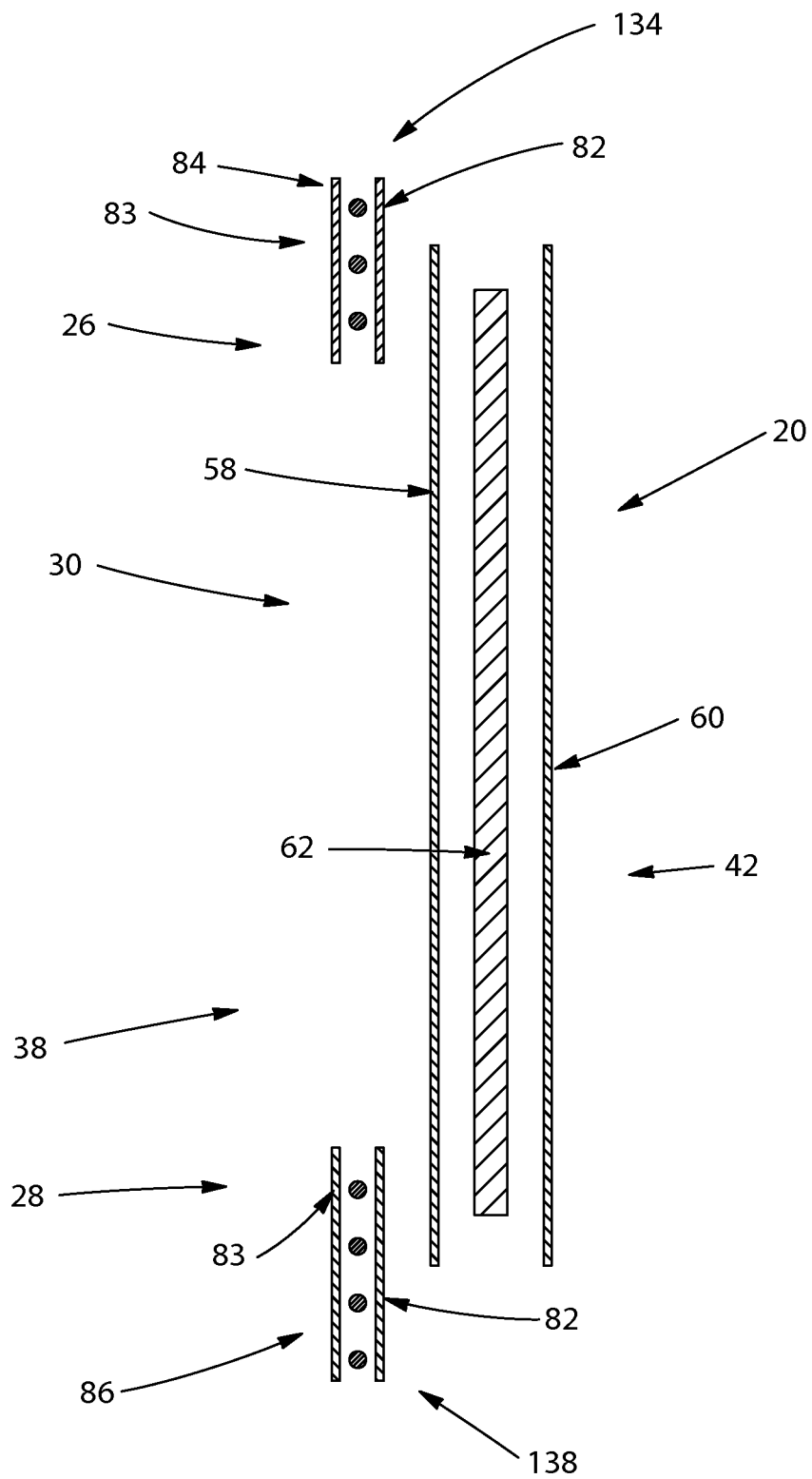
FIG. 4A is a schematic cross section view of a first embodiment taken along line 4-4 in FIG. 3 of an exemplary disposable pull-on garment.
Figure 4B:
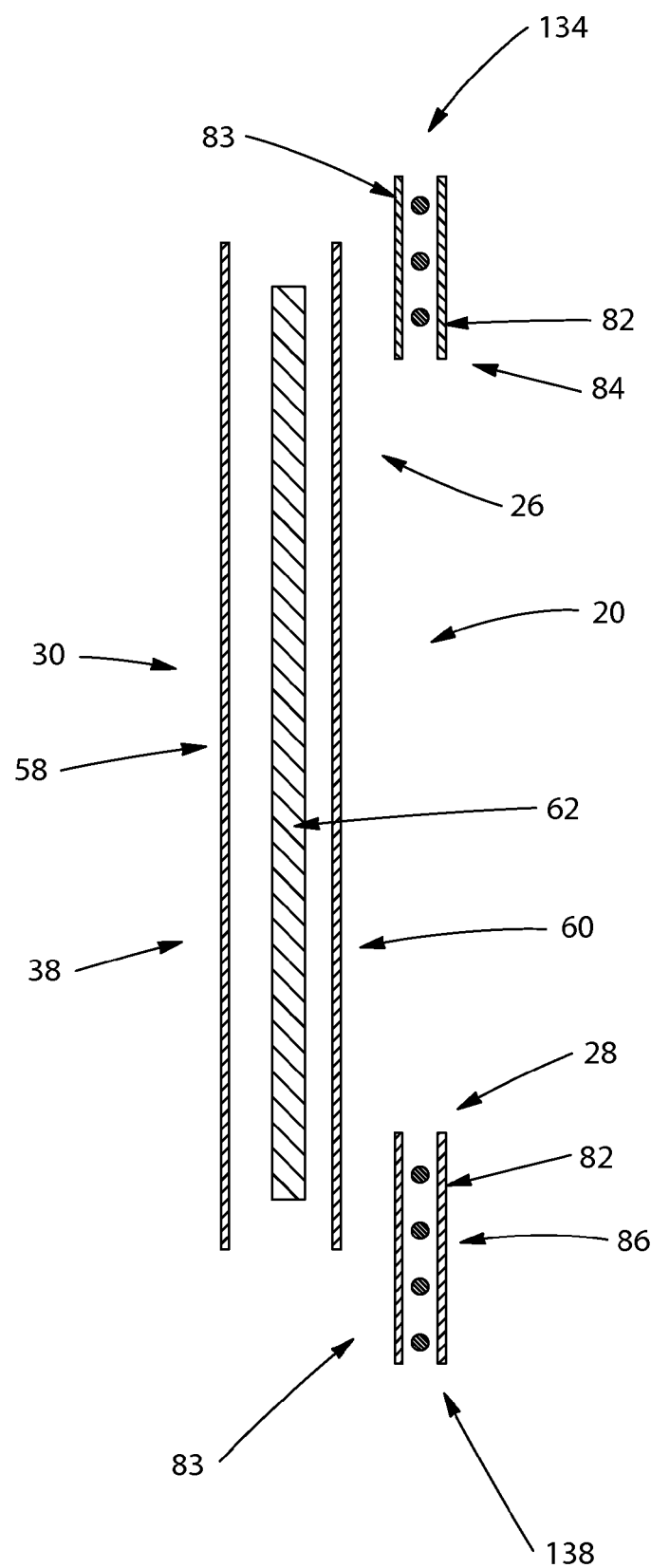
FIG. 4B is a schematic cross section view of a second embodiment taken along line 4-4 in FIG. 3 of an exemplary disposable pull-on garment.

In the embodiment shown in FIGS. 4A and 4B, the absorbent articles 20 may comprise front and rear belts 84, 86 intended to encircle at least a portion of the waist of the wearer, the front and rear belt portions 84, 86 being connected by a main body 38 forming the crotch region 30 of the absorbent article 20. The front and rear belts 84 and 86 may be formed from a first belt layer forming a portion of the outer surface 22 of the absorbent article, the first belt layer 82 may be formed of two longitudinally spaced webs of material. The front and rear belts 84 and 86 may also comprise a second belt layer 83 forming a portion of the inner surface 24 of the absorbent article 20, the second belt layer 83 may also be formed of two longitudinally spaced webs of material. The second belt layer may also be discontinuous and spaced apart in a transverse direction. The first and second belt layers 82, 83 may be formed of substantially the same material or may comprise different materials. The first and second belt layers 82, 83 may be formed from nonwovens, films, foams, elastic nonwoven, or combinations thereof. The front and rear belts 84, 86 may also comprise an elastomeric material disposed between the first and second belt layers 82, 83. The elastomeric material may comprise one or more elastic strands, elastomeric films, elastomeric ribbons, elastomeric nonwovens, elastomeric filaments, elastomeric adhesives, elastomeric foams, scrims or combinations thereof. A portion of the elastomeric material may be directly combined with the outer cover layer. The main body 38 of the absorbent article may comprise an outer surface 22, backsheet 60, an inner surface 24, topsheet 58, and an absorbent core 62 disposed between the topsheet 58 and the backsheet 60. The backsheet may be formed of a nonwoven material, woven material, films or laminates comprising a combination of one or more of these materials. In one embodiment the backsheet is a film and nonwoven laminate wherein the nonwoven of the laminate is the outer cover layer. In addition, the main body 38 may comprise elasticized barrier leg cuffs 64 disposed at or adjacent the side edges of the main body. The front and rear belts 84, 86 may overlap at least a portion of the main body and one or both of the belt portions may be disposed on the outer surface of the main body or alternatively on the inner surface of the main body. A portion of the second belt layer and/or a portion of the first belt layer may be directly attached to the outer cover layer. Alternatively, the front belt and rear belt 84, 86 may comprise longitudinally spaced webs of material forming a first surface of the belt wherein the webs are folded along the waist edge, or alternatively the leg opening edge, of the belt to wrap the elastomeric material and form at least a portion of the second surface of the belt. In other words, at least a portion of the inner surface and outer surface of each of the belt portions may be formed from a single web of material.

Figure 4C:
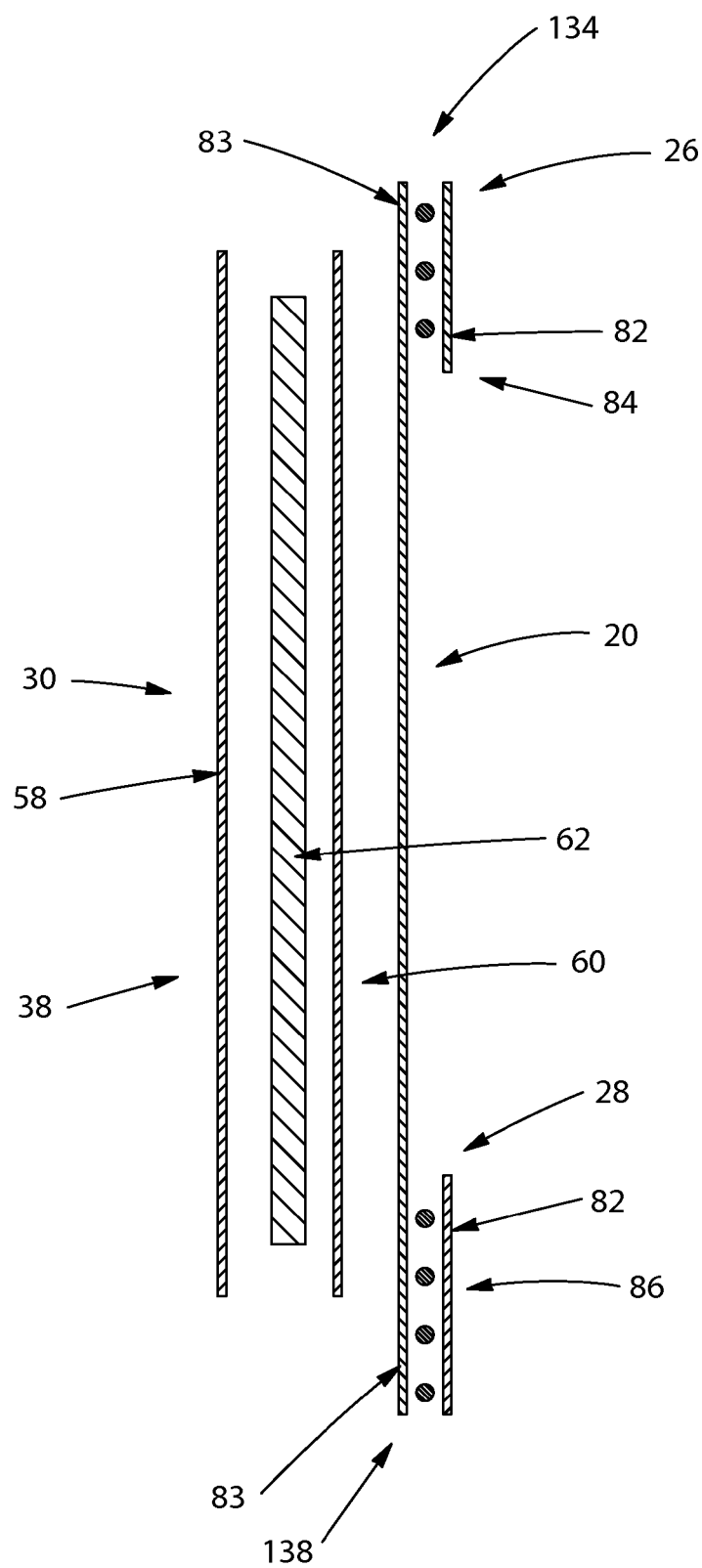
FIG. 4C is a schematic cross section view of a third embodiment taken along line 4-4 in FIG. 3 of an exemplary disposable pull-on garment.
Figure 4D:
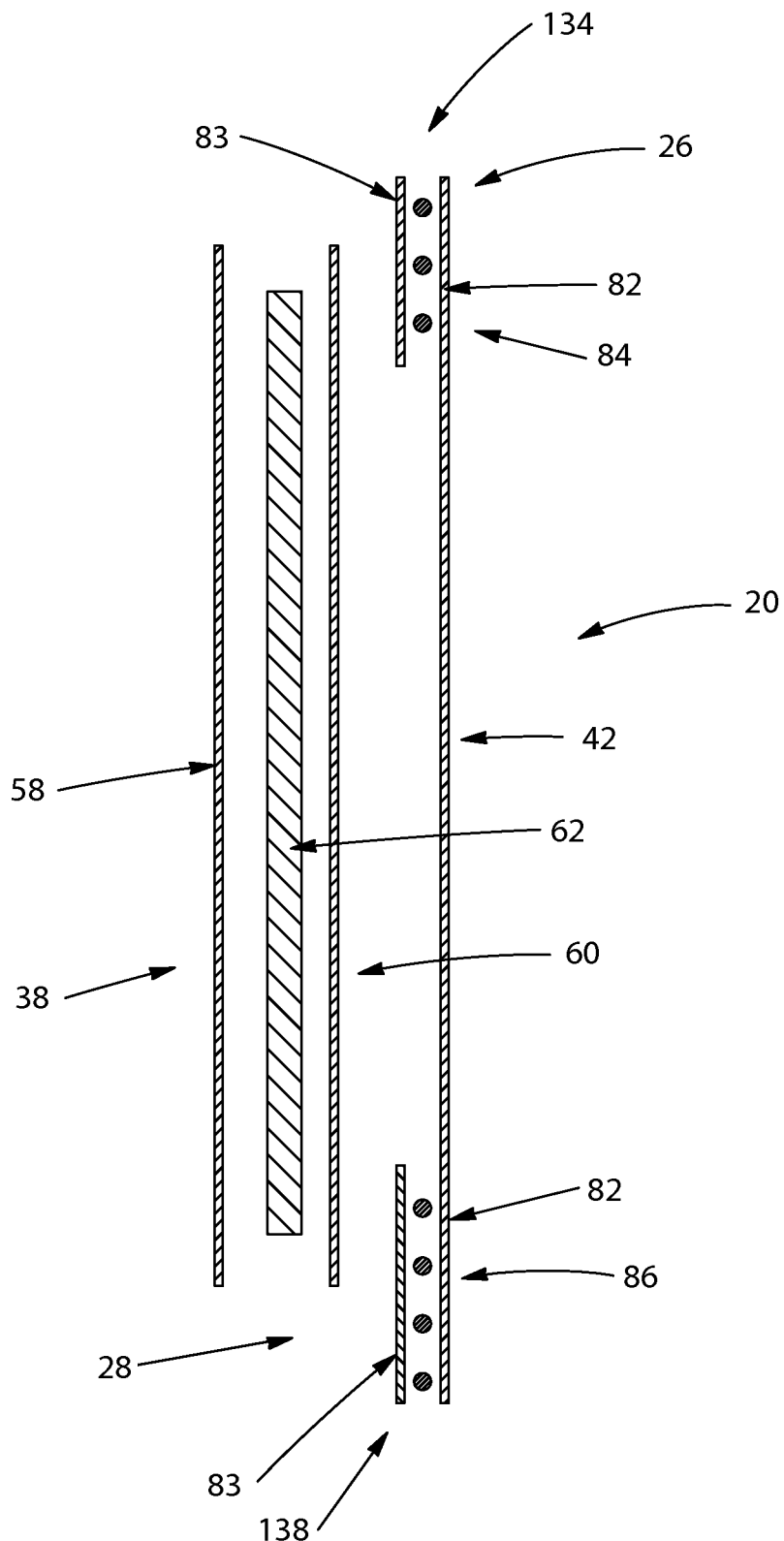
FIG. 4D is a schematic cross section view of a fourth embodiment taken along line 4-4 in FIG. 3 of an exemplary disposable pull-on garment.

In the embodiment shown in FIGS. 4C and 4D, the absorbent articles 20 may comprise front and rear extensible belts 84, 86 disposed in the front and rear waist regions 26, 28 respectively and intended to encircle at least a portion of the waist of the wearer, the front and rear belts 84, 86 being connected by the main body that forms the crotch region 30 of the article. The first and second belt may be formed from a first belt layer extending from a first waist edge 134 in a first waist region 26 through the crotch region to a longitudinally opposing second waist edge 138 in a second waist region 28 and forming a portion of the outer surface of the absorbent article 20. The front and rear belts 84, 86 also may comprise a second belt layer forming a portion of the inner surface 24 of the absorbent article, the second belt layer may be formed of two longitudinally spaced webs of material. The first and second belt portions may also comprise an elastomeric material disposed between the first and second belt layers. The elastomeric material may comprise elastic strands, elastomeric films, elastomeric ribbons, elastomeric nonwovens, elastomeric filaments, elastomeric adhesives, elastomeric foams, scrims or combinations thereof. The main body 38 of the absorbent article may comprise an outer surface 22, backsheet 60, an inner surface 24, topsheet 58, and an absorbent core 62 disposed between the topsheet 58 and the backsheet 60. The first belt layer may form a portion of the outer surface 22. In addition, the main body may comprise elasticized barrier leg cuffs 64 disposed at or adjacent the side edges of the main body. The second belt layer may overlap at least a portion of the main body and one or both of the second belt layer webs may form the outer surface of the first belt layer or alternatively the inner surface of the first belt layer. Alternatively, the front portion and/or the rear portion of the first belt layer may be folded along the waist edge of the belt region to wrap the elastomeric material and form a portion of the second belt layer of one or both of the front and rear belt portions 84, 86. In other words, the inner surface and outer surface of each of the belt portions is formed from a single web of material.

Figure 4E:
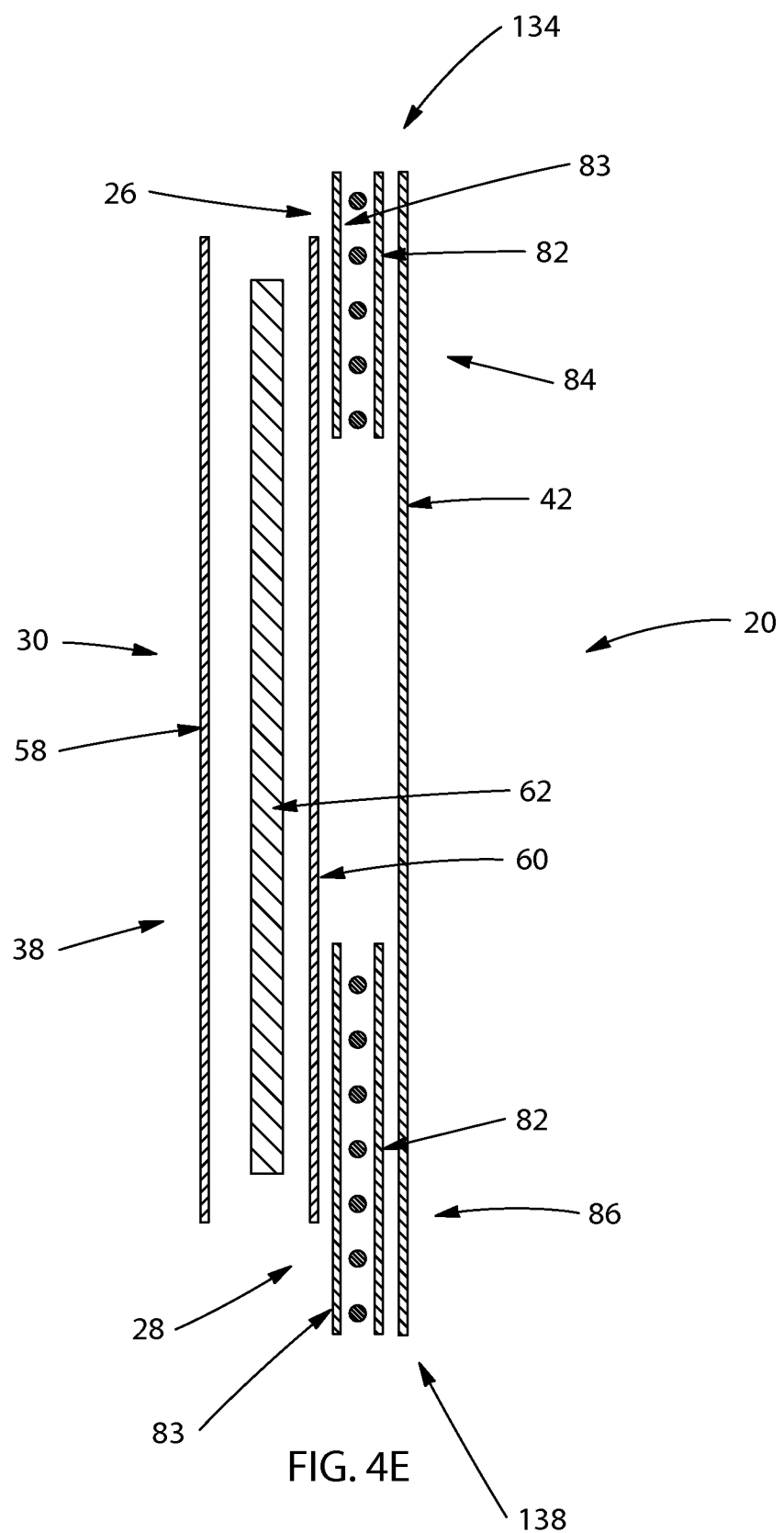
FIG. 4E is a schematic cross section view of a sixth embodiment taken along line 4-4 in FIG. 3 of an exemplary disposable pull-on garment.
Figure 4F:
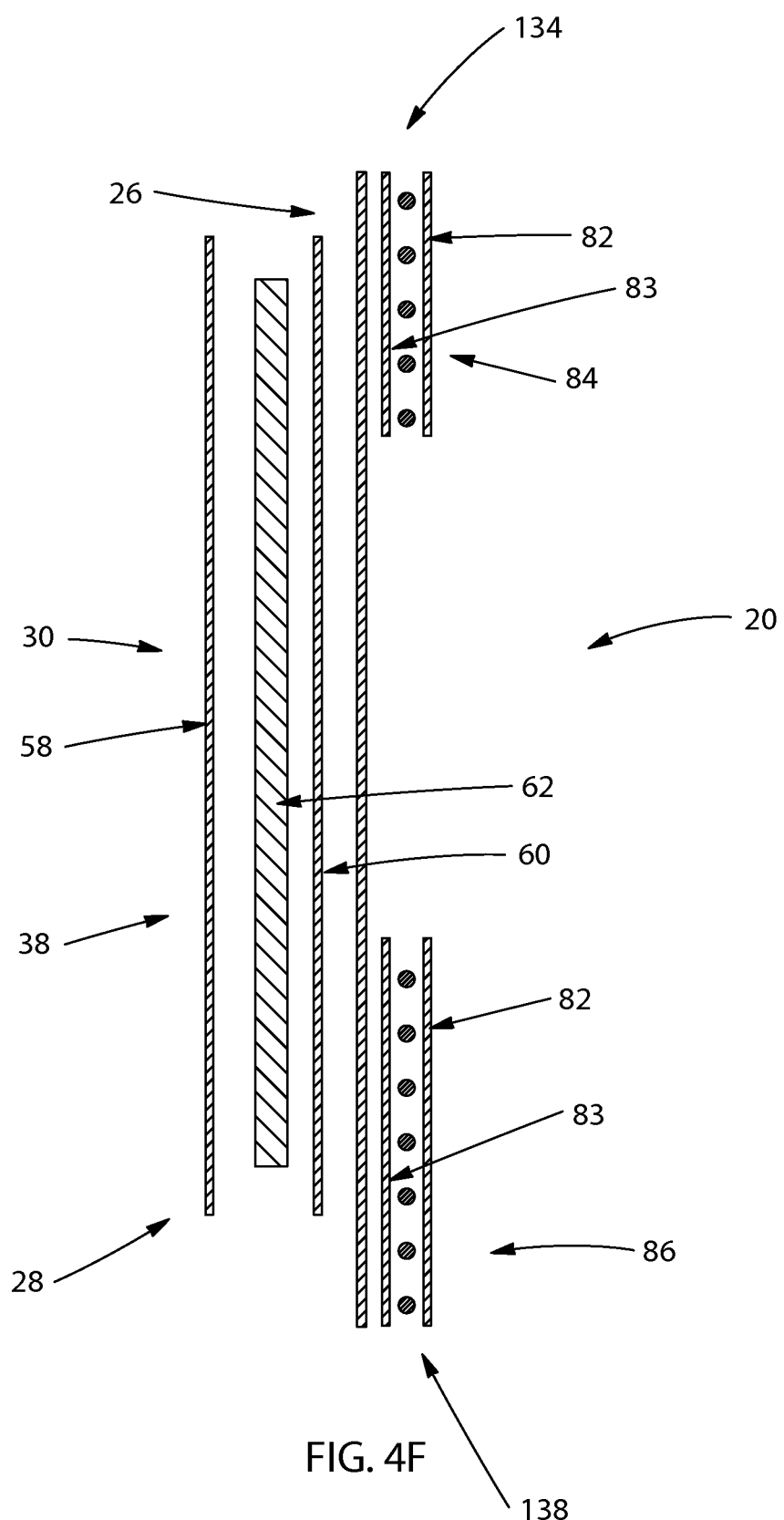
FIG. 4F is a schematic cross section view of a seventh embodiment taken along line 4-4 in FIG. 3 of an exemplary disposable pull-on garment.

In the embodiment shown in FIGS. 4E and 4F, the absorbent articles 20 may comprise a full outer cover layer 42, extending from a front waist edge 134 in a first waist region 26, through the crotch region to the longitudinally opposing rear waist edge 138 in a second waist region 28. The article may also comprise front and rear belts 84, 86 intended to encircle the waist of the wearer, the front and rear belts 84, 86 being connected to the outer cover layer 42 and/or the main body 38 of the absorbent article 20. The first and second belts are formed from a first belt layer forming a portion of the outer surface of the belt, the first belt layer being formed of two longitudinally spaced webs of material. The first and second belt portions also comprise a second belt layer forming a portion of the inner surface of the absorbent article, the second belt layer also being formed of two longitudinally spaced webs of material. The first and second belt layers may be formed of substantially the same material or may comprise different materials. The first and second belt layers may be formed from nonwovens, films, foams or combinations thereof. The first and second belts may also comprise an elastomeric material disposed between the first and second belt layers. The elastomeric material may comprise elastic strands, elastomeric films, elastomeric ribbons, elastomeric nonwovens, elastomeric filaments, elastomeric adhesives, elastomeric foams, scrims or combinations thereof. The first and second belts may be disposed on the interior surface of the outer cover layer. Alternatively, the first and second belts may be disposed on the outer surface of the outer cover layer. In such an embodiment the outer cover layer would for a portion of the inner surface of the article in the waist regions and the first belt layer would form a portion of the outer surface of the article. The second belt layer when present may be disposed between the first belt layer and the outer cover layer. The main body 38 of the absorbent article 20 may comprise an outer surface 22, backsheet 60, an inner surface 24, topsheet 58, and an absorbent core 62 disposed between the topsheet 58 and the backsheet 60. In addition, the main body 38 may comprise elasticized barrier leg cuffs 64 disposed at or adjacent the side edges of the main body 38. One or both of the front and rear belts 84, 86 may overlap at least a portion of the main body 38 and one or both of the belts may be disposed on the outer surface of the main body 38 or alternatively on the inner surface of the main body 38. One or both of the front and rear belts 84, 86 may be disposed on the interior surface of the outer cover layer or alternatively one or both of the belts may be disposed on the exterior surface of the outer cover layer. One or both of the front belt and rear belt 84, 86 may comprise longitudinally spaced webs of material forming a first surface of the belt wherein the webs are folded along the waist edge 36 of the belt to wrap the elastomeric material and form at least a portion of the second surface of the belt. In other words, a portion or the entirety of the inner surface and outer surface of one or both of the belt portions may be formed from a single web of material. The rugosities, wrinkles, folds in one or both of the front and rear belts may have a different configuration, size, orientation, shape, etc. than that of the outer cover layer.

Figure 4G:
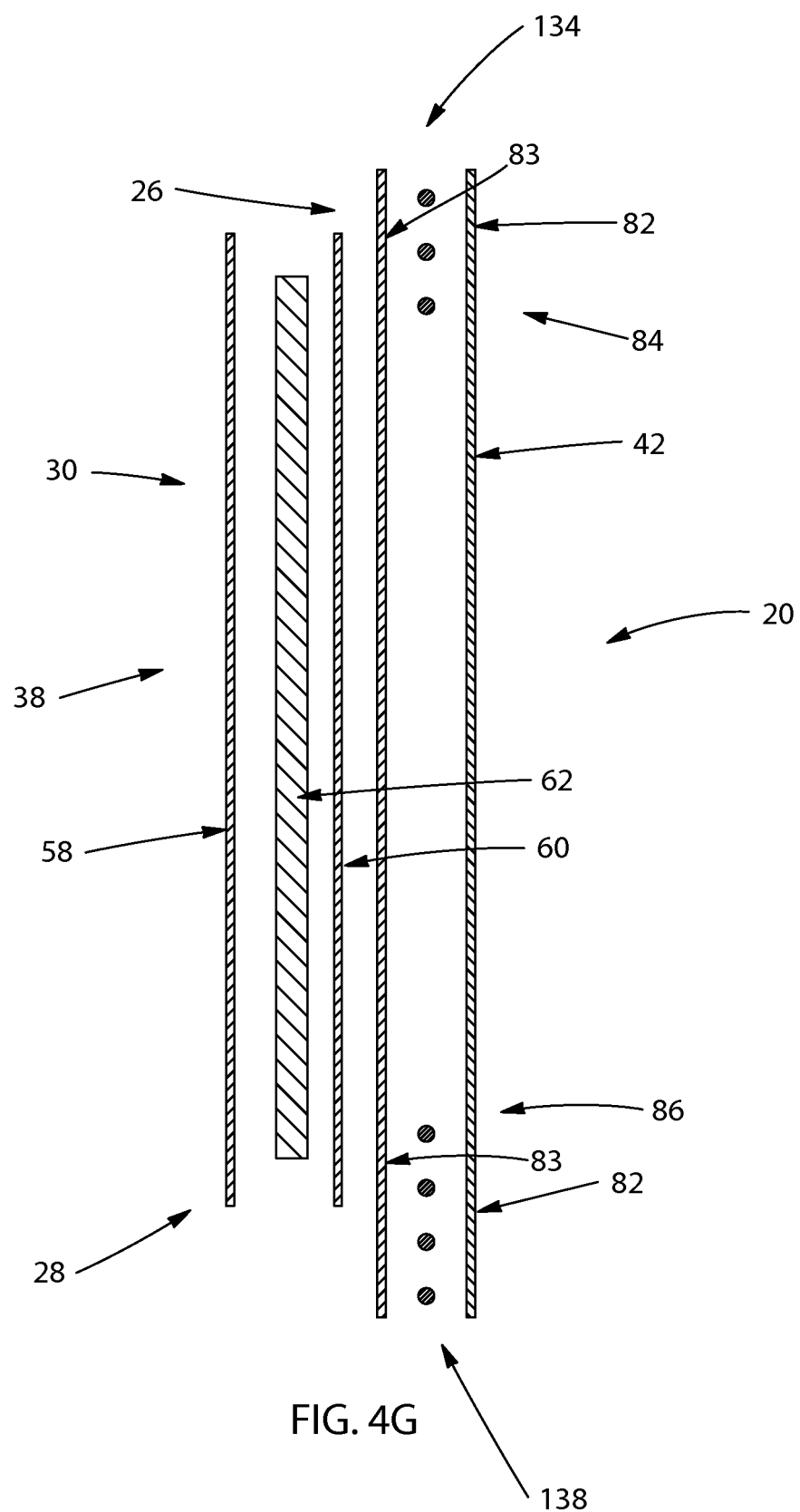
FIG. 4G is a schematic cross section view of an eight embodiment taken along line 4-4 in FIG. 3 of an exemplary disposable pull-on garment.

In the embodiment shown in FIG. 4G, the absorbent articles 20 may comprise front and rear belts 84, 86 intended to encircle at least a portion of the waist of the wearer, the front and rear belts 84, 86 being connected to a main body 38 forming a portion of the crotch region 30 of the absorbent article 20. The front and rear belts 84, 86 are formed from a first belt layer 82 forming a portion of the outer surface of the absorbent article. The front and rear belt portions 84, 86 also comprise a second belt layer 83 forming a portion of the inner surface 24 of the absorbent article 20. The second belt layer may be laterally discontinuous and spaced apart in a transverse direction. The first and second belt layers 82, 83 may be formed of substantially the same material or may comprise different materials. The first and second belt layers 82, 83 may be formed from nonwovens, films, foams or combinations thereof. The front and rear belt portions 84, 86 may also comprise an elastomeric material disposed between the first and second belt layers 82, 83. The elastomeric material may comprise elastic strands, elastomeric films, elastomeric ribbons, elastomeric nonwovens, elastomeric filaments, elastomeric adhesives, elastomeric foams, scrims or combinations thereof. A portion of the elastomeric material may be directly combined with the outer cover layer. The main body 38 of the absorbent article may comprise an outer surface 22, backsheet 60, an inner surface 24, topsheet 58, and an absorbent core 62 disposed between the topsheet 58 and the backsheet 60. In certain embodiments the backsheet may be a nonwoven and film laminate wherein the nonwoven is formed by the outer cover layer. In addition, the main body 38 may comprise elasticized barrier leg cuffs 64 disposed at or adjacent the side edges of the main body 38. The front and rear belts 84, 86 overlap at least a portion of the main body 38 and one or both of the belts may be disposed on the outer surface of the main body 38. A portion of the second belt layer and/or a portion of the first belt layer may be directly attached to the outer cover layer. The front and rear belts 84, 86 may be formed from a first belt layer extending from a first waist edge 134 in a first waist region 26 through the crotch region to a second waist edge 138 in a second waist region 28 and forming a portion of the outer surface of the absorbent article 20. The front and rear belts 84, 86 may also comprise a second belt layer extending from a first waist edge 134 in a first waist region 26 through the crotch region to a second waist edge 138 in a second waist region 28 and forming a portion of the inner surface of the absorbent article 20. The first and second belt layers may be formed of substantially the same material or may comprise different materials. The first and second belt layers may be formed from nonwovens, films, foams, woven materials or combinations thereof. The front and rear belt portions 84, 86 may also comprise an elastomeric material disposed between the first and second belt layers in one or both of the first and second waist regions 26, 28. The elastomeric material may comprise elastic strands, elastomeric films, elastomeric ribbons, elastomeric nonwovens, elastomeric filaments, elastomeric adhesives, elastomeric foams, scrims or combinations thereof. The main body 38 of the absorbent article 20 may comprise an outer surface 22, backsheet 60, an inner surface 24, topsheet 58, and an absorbent core 62 disposed between the topsheet 58 and the backsheet 60. One or both of the first and second belt layers may form a portion of the outer surface 22. In addition, the main body 38 may comprise elasticized barrier leg cuffs 64 disposed at or adjacent the side edges of the main body 38. A portion of one or both of the front and rear belts 84, 86 may overlap at least a portion of the main body 38. Alternatively, the front belt portion and rear belts 84, 86 may comprise a belt layer forming a first surface of the belt portion wherein the belt layer may be folded along the waist edge of the belt portion to wrap the elastomeric material and overlap a portion of the opposing belt layer. In other words, a portion of the inner surface and a portion of the outer surface of each of the belt portions may be formed from a single web of material.

A portion or the whole of the main body 38 may be made extensible to a degree greater than the inherent extensibility of the material or materials from which the main body 38 is made, e.g., the backsheet 60. The additional extensibility may be desirable in order to allow the main body 38 to conform to the body of a wearer during movement by the wearer and or to provide adequate body coverage. The additional extensibility may also be desirable, for example, in order to allow the user of a absorbent article including a main body 38 having a particular size before extension to extend the front waist region 26, the back waist region 28, or both waist regions of the main body 38 to provide additional body coverage for wearers of differing size, i.e., to tailor the article to the individual wearer. Such extension of the waist region or regions may give the main body 38 a generally hourglass shape, so long as the crotch region is extended to a relatively lesser degree than the waist region or regions, and may impart a tailored appearance to the article when it is worn. In addition, the additional extensibility may be desirable in order to minimize the cost of the article 10. For example, an amount of material that would otherwise be sufficient only to make a relatively smaller article lacking this extensibility can be used to make an article capable of being extended to adequately cover a wearer that is larger than the unextended smaller absorbent article would fit.

A portion of the main body 38, for example a portion of the chassis in one or both of the waist regions 26, 28 may be made laterally extensible to a maximum extensibility greater than a maximum extensibility of another portion of the main body 38 in the crotch region such that a lateral extension of each of the portions to its maximum extensibility imparts an hourglass shape to the main body 38. In one embodiment, the portion of the main body 38 underlying and/or immediately adjacent one or both of the front and back extensible belts may be made laterally extensible to a maximum extensibility greater than a maximum extensibility of another portion of the main body 38, for example the crotch region, such that a lateral extension of each of the portions to its maximum extensibility facilitates application of the absorbent article onto the body of a wearer by enabling the waist regions to be extended to fit over the wearer's hips and in addition, opening and orienting the leg openings enabling the wearer to place the legs through the openings more effectively.

Additional lateral extensibility in the main body 38 may be provided in a variety of ways. For example, a material or materials from which the main body 38 is made may be pleated by any of many known methods. Alternatively, all or a portion of the main body 38 may be made of a formed web material or a formed laminate of web materials like those described in U.S. Pat. No. 5,518,801 issued on 21 May 1996 in the name of Chappell et al. This formed web material includes distinct laterally extending regions in which the original material has been altered by embossing or another method of deformation to create a pattern of generally longitudinally oriented alternating ridges and valleys and also includes laterally extending unaltered regions between the laterally extending altered regions. The formed web material can be extended in a direction perpendicular to the ridges up to the point where the ridges and valleys flatten with substantially less force than is required to extend beyond that point. In addition to lateral extensibility, the creation of a formed laminate web as described above provides a main body 38 backsheet with improved texture and cloth-like appearance and feel. The deformation creates a cloth-like pattern in the film and increases the loft of the nonwoven in multi-layer film and nonwoven laminate backsheets.

Alternatively, a portion of the absorbent article can be ring-rolled and thus rendered highly extensible as described in U.S. Pat. No. 5,366,782 (issued Nov. 22, 1994 to Curro, et al). Specifically, a ring-rolling apparatus includes opposing rolls having intermeshing teeth that incrementally stretch and thereby plastically deform the material forming the absorbent article (or a portion thereof) thereby rendering the article extensible in the ring-rolled regions. In one embodiment, the absorbent article can be ring-rolled in a portion of at least one of the front or back waist regions, for example the portion of the main body 38 underlying and/or immediately adjacent one or both of the front and back belts 84, 86, while other regions may comprise a structured elastic-like formed web material. The article may be ring-rolled across the entire width in one or both of the waist regions or alternatively may be ring-rolled over only a portion of the main body 38 width or over only a portion of one or both of the belts.

The front laterally central portion and the back laterally central portion of the main body 38 may have a different range of extensibility from other portions of the main body 38. Additionally or alternatively, the laterally central portions may be extensible to a greater or lesser degree when subjected to a given level of opposing tensile forces, i.e., may be more easily or less easily extensible, than other portions of the main body 38.

Figure 5:
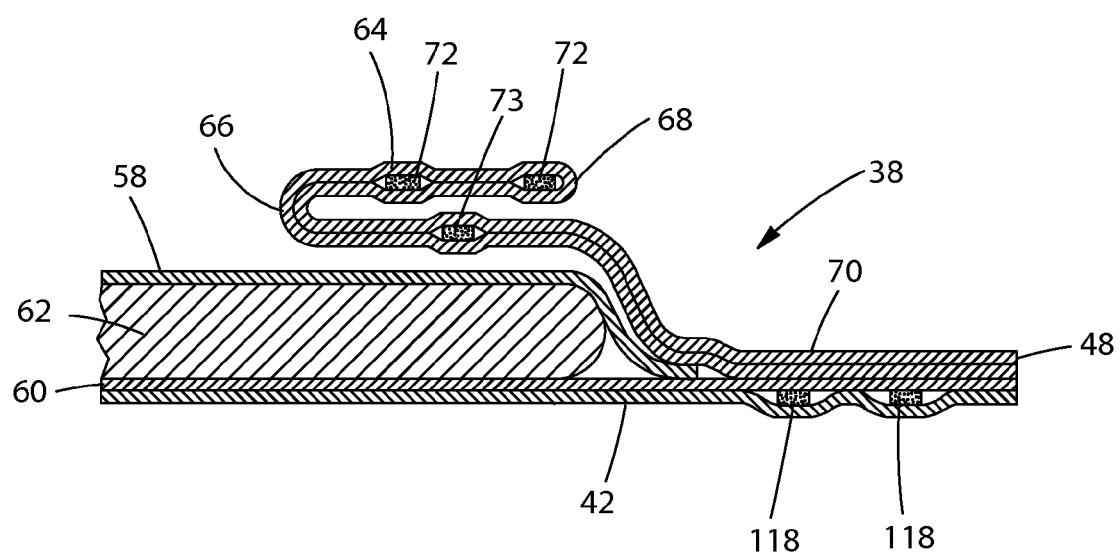
FIG. 5 is a schematic cross section view taken along line 5-5 in FIG. 3 of an example of a folded outer leg cuff suitable in one embodiment of the invention.

The main body 38 may comprise a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 5 comprises a single layer of material which may be folded to form a barrier leg cuff having two layers. The barrier leg cuff 64 extends from the side of the main body at or adjacent the longitudinal side edge 48 toward the longitudinal centerline L2. The barrier leg cuff may be folded along the folding line 66 back toward the longitudinal side edge 48. The barrier leg cuff 64 may have a first barrier cuff elastic material 72 adjacent to the distal portion 68 and a second barrier cuff elastic material 73 adjacent to the proximal portion 70 of the barrier leg cuff 64. The proximal portion 70 of the barrier leg cuff 64 may be joined to the backsheet 60 adjacent to the longitudinal side edge 48. The portion of the barrier leg cuff 64 along the folding line 66 and the distal portion 68 may be free from attachment to any portion of the main body 38 in the crotch region 30 such that the barrier leg cuff 64 stands up toward the wearer's body. The transverse end 74 of the barrier leg cuff 64 may be joined to the topsheet 58 at or adjacent the longitudinally opposing ends of the leg cuff by an attachment means which may be any known means such as an adhesive, heat bond, pressure bond or the like as shown in 5.

The liquid pervious topsheet 58 may be positioned adjacent the body-facing surface of the absorbent core 62 and may be joined thereto and/or to the backsheet 60 by any attachment means known in the art. The liquid impervious backsheet 60 is generally that portion of the absorbent article 20 positioned adjacent the garment-facing surface of the absorbent core 62 and prevents the exudates absorbed and contained therein from soiling articles that may contact the absorbent article 20. The absorbent core is positioned between the topsheet 58 and the backsheet 60 and absorbs and retains liquids such as urine and other certain body exudates.

The topsheet 58, the backsheet 60 and the absorbent core may be manufactured any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet.

A suitable absorbent core for use in the absorbent article 20 may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some embodiments, the absorbent core may comprise a fluid acquisition component, a fluid distribution component, and a fluid storage component. An example of a suitable absorbent core having a fluid acquisition component, a fluid distribution component, and a fluid storage component is described in U.S. Pat. No. 6,590,136.

The outer cover layer 42 may be disposed on the outer surface 22 of the absorbent article 20 and covers the crotch panel 56 of the absorbent main body 38. The outer cover layer 42 may extend into and cover the front waist panel 52 and the back waist panel 54 of the main body 38. The outer cover layer may form a portion of the backsheet and/or the main body. The outer cover layer 42 may be directly joined to and cover a portion or all of the liquid impervious backsheet 60 of the main body 38. The central panel 80 of the front and back belt 84, 86 may be joined to the front waist panel 52 and the back waist panel 54 of the main body 38 through the outer cover layer 42. Thus, the outer cover layer 42 is disposed between the front and back belt 84, 86 and the liquid impervious backsheet 60 of the main body 38. In one embodiment shown in FIGS. 2 and 4C, the outer cover layer 42 is coextensive with the liquid impervious backsheet 60. The leg elastic material 140 is disposed so as to extend generally longitudinally along the longitudinal side edge 48 of the main body 38. The leg elastic material 140 may be disposed at least in the crotch region 30 of the absorbent article 20 or may be disposed along the entirety of the longitudinal side edge 48.

The outer cover layer 42 may comprise a material separate from the material of the inner layer 83 and the outer layer 82 constituting the belt 40. The outer cover layer 42 may comprise two or more layers of materials. The outer cover layer 42 may comprise any known materials and may comprise materials used for the front and back belt 84, 86 as explained above. The outer cover layer 42 may comprise a single layer of nonwoven web of synthetic fibers. The outer cover layer 42 may comprise a single layer of hydrophobic, non-stretchable nonwoven material. The outer cover layer may comprise a film, a foam, a nonwoven, a woven material or the like and/or combinations thereof such as a laminate of a film and a nonwoven.

The belt 40 may comprise a front belt 84 and a back belt 86 (hereinafter may be referred to as "front and back belt 84, 86") and has a ring-like configuration by permanently or refastenably connecting the front belt 84 and the back belt 86 at the seams 32 or by permanently or refastenably connecting the front and/or back belt to the main body 38.

The belt 40 may be ring-like and elastic. The ring-like elastic belt 40 extends transversely about the waist opening 36 of the absorbent article 20 and acts to dynamically create fitment forces and to distribute the forces dynamically generated during wear. Applicants have found that improved fit can be created by controlling the distance between, linear density, and the pre-strain of the elastomeric material in relation to each other and to the openings for the body. This may occur by choosing different materials throughout the belt 40 that exhibit desired properties. The different materials are combined at specific distances, linear densities, and pre-strains to create a belt 40 that acts to dynamically create fitment forces. This improved fit translates into reduced sagging and or gapping problems around the waist opening. The examples below illustrate various properties of the different portions of the belt embodiments:

Example 1

The Dimensions of Sections

|  | Width of each section relative to product length (%) |
|---|---|
| First elastic section (102) | 5-25% |
| Second elastic section (104) | 5-20% |
| Third elastic section (106) | 10-30% |
| Fourth elastic section (108) | 10-25% |

Example 2

The Dimensions of the Force Zones

| Force zones from front Waist edge to front leg edge | Pre-strain (%) | Dtex | Range Distance from waist edge in mm |
|---|---|---|---|
| 1st force zone 110 | 100-250 | 540-1100 | 0-50 |
| 2nd force zone 112 | 150-300 | 680-1880 | 10-100 |
| 3rd force zone 114 | 100-300 | 540-1100 | 30-180 |
| 4th force zone 116 | 100-300 | 540-1100 | 33-200 |
| 5th force zone 118 | 150-300 | 680-1880 | 50-220 |
| 6th force zone 120 | 100-300 | 540-1100 | 80-235 |

| Force zones from back leg edge to waist edge | Pre-strain (%) | Dtex | Range Distance from back leg edge in mm |
|---|---|---|---|
| 7th force zone 122 | 100-300 | 540-1100 | 0-50 |
| 8th force zone 124 | 150-300 | 650-1880 | 10-100 |
| 9th force zone 126 | 100-300 | 540-1880 | 30-150 |
| 10th force zone 128 | 100-300 | 540-1880 | 35-200 |
| 11th force zone 130 | 100-300 | 940-1880 | 50-270 |
| 12th force zone 132 | 100-300 | 540-1880 | 80-340 |

Example 3

Elastic Strands in the Belt and their Properties in Baby Care Products

| Elastic Number from front Waist edge to front leg edge | Pre-strain (%) | Dtex | Range Distance from waist edge in mm |
|---|---|---|---|
| 1 | 202 | 940 Dtex | 0-10 |
| 2 | 202 | 940 Dtex | 15-20 |
| 3 | 202 | 940 Dtex | 25-30 |
| 4 | 202 | 940 Dtex | 47-52 |
| 5 | 168 | 540 Dtex | 56-61 |
| 6 | 168 | 540 Dtex | 65-70 |
| 7 | 168 | 540 Dtex | 74-79 |
| 8 | 168 | 540 Dtex | 83-88 |
| 9 | 168 | 540 Dtex | 92-97 |
| 10 | 168 | 540 Dtex | 101-106 |
| 11 | 168 | 540 Dtex | 110-115 |
| 12 | 168 | 540 Dtex | 119-124 |
| 13 | 168 | 540 Dtex | 127-133 |

| Elastic number from back leg edge to waist edge | Pre-strain (%) | Dtex | Range Distance from back leg edge in mm |
|---|---|---|---|
| 29 | 261 | 1100 Dtex | 0-10 |
| 28 | 261 | 540 Dtex | 15-20 |
| 27 | 261 | 540 Dtex | 24-29 |
| 26 | 168 | 540 Dtex | 33-38 |
| 25 | 250 | 940 Dtex | 52-57 |
| 24 | 250 | 940 Dtex | 61-66 |
| 23 | 250 | 940 Dtex | 71-76 |
| 22 | 168 | 540 Dtex | 80-85 |
| 21 | 168 | 540 Dtex | 89-94 |
| 20 | 168 | 540 Dtex | 98-103 |
| 19 | 168 | 540 Dtex | 107-112 |
| 18 | 104 | 1520 Dtex | 116-121 |
| 17 | 104 | 1520 Dtex | 125-130 |
| 16 | 104 | 1520 Dtex | 134-139 |
| 15 | 202 | 940 Dtex | 143-148 |
| 14 | 202 | 940 Dtex | 151-156 |

Example 4

Elastic Strands in the Belt and their Properties in Baby Care Products

| Elastic Number from front Waist edge to front leg edge | Pre-strain (%) | Dtex | Range Distance from waist edge in mm |
|---|---|---|---|
| 1 | 215 | 1100 Dtex | 0-10 |
| 2 | 215 | 1100 Dtex | 15-20 |
| 3 | 215 | 1100 Dtex | 25-30 |
| 4 | 215 | 1100 Dtex | 47-52 |
| 5 | 150 | 880 Dtex | 56-61 |
| 6 | 150 | 880 Dtex | 65-70 |
| 7 | 150 | 1000 Dtex | 74-79 |
| 8 | 150 | 1000 Dtex | 83-88 |
| 9 | 150 | 1000 Dtex | 92-97 |
| 10 | 150 | 1000 Dtex | 101-106 |
| 11 | 150 | 880 Dtex | 110-115 |
| 12 | 150 | 880 Dtex | 119-124 |
| 13 | 150 | 880 Dtex | na |

| Elastic number from back leg edge to waist edge | Pre-strain (%) | Dtex | Range Distance from back leg edge in mm |
|---|---|---|---|
| 29 | 150 | 1000 Dtex | 0-10 |
| 28 | 150 | 750 Dtex | 15-20 |
| 27 | 150 | 750 Dtex | 24-29 |
| 26 | 150 | 750 Dtex | 33-38 |
| 25 | 200 | 1100 Dtex | 52-57 |
| 24 | 200 | 1100 Dtex | 61-66 |
| 23 | 200 | 1100 Dtex | 71-76 |
| 22 | 150 | 750 Dtex | 80-85 |
| 21 | 150 | 750 Dtex | 89-94 |
| 20 | 150 | 750 Dtex | 98-103 |
| 19 | 150 | 750 Dtex | 107-112 |
| 18 | 200 | 1800 Dtex | 116-121 |
| 17 | 200 | 1800 Dtex | 125-130 |
| 16 | 200 | 1800 Dtex | 134-139 |
| 15 | 150 | 1000 Dtex | 143-148 |
| 14 | 150 | 1000 Dtex | 151-156 |

The front and back belt 84, 86 may comprise any known materials. Suitable material for the front and back belt 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. The belt may comprise a nonwoven web of synthetic fibers. The belt may comprise a stretchable nonwoven. The belt may comprise an inner hydrophobic, non-stretchable nonwoven material and an outer hydrophobic, non-stretchable nonwoven material.

The belt 40 may comprise a first elastic section 102 and a second elastic section 104 located in the front belt 84. The belt 40 may comprise a third elastic section 106 and a fourth elastic section 108 located in the back belt 86. The first elastic section 102 and the fourth elastic section 108 are adjacent to the waist opening 36. The second elastic section 104 and the third elastic section 106 are adjacent to the leg openings 34. The first elastic section 102 may comprise of 20 percent to 80 percent, 25 percent, 40 percent, 50 percent, 60 percent, 70 percent of the longitudinal direction length of the front belt 84. The second elastic section 104 may comprise of 20 percent to 80 percent, 25 percent, 40 percent, 50 percent, 60 percent, 70 percent of the longitudinal direction length of the front belt 84. The third elastic section 106 may comprise of 20 percent to 80 percent, 25 percent, 40 percent, 50 percent, 60 percent, 70 percent of the longitudinal direction length of the back belt 86. The fourth elastic section 108 may comprise of 20 percent to 80 percent, 25 percent, 40 percent, 50 percent, 60 percent, 70 percent of the longitudinal direction length of the back belt 86.

The belt 40 may comprise a front border between the first elastic section 102 and a second elastic section 104, and the front border may be located within 5 mm, 10 mm, 20 mm, 30 mm 40 mm, 50 mm from the front edge of the absorbent core. The belt 40 may comprise a back border between the third elastic section 106 and a fourth elastic section 108, and the back border may be located within 5 mm, 10 mm, 20 mm, 30 mm 40 mm, 50 mm from the back edge of the absorbent core.

The belt 40 may comprise a first force zone 110, a second force zone 112, a third force zone 114, a fourth force zone 116, a fifth force zone 118, and a sixth force zone 120 located in the front belt 84. The first force zone 110, second force zone 112, and third force zone 114 may be located in the first elastic section 102. The fourth force zone 116, fifth force zone 118, and sixth force zone 120 may be located in the second elastic section 104. The first force zone 110, second force zone 112, third force zone 114, fourth force zone 116, fifth force zone 118 and sixth force zone 120 may comprise a transverse force of 0 to 10N/zone. The force in a zone may also change between the center of the belt 40 and the left and right longitudinally extending side edges 48.

The first force zone 110 is disposed adjacent to the waist opening 36. The sixth force zone 120 is disposed adjacent to the leg opening 34. The first force zone 110, second force zone 112, and at least part of the third force zone 114 are located within upper two thirds of the front belt width, toward the waist opening along the longitudinal axis. At least part of the fourth force zone 116, fifth force zone 118, and sixth force zone 120 are located within lower two third of the front belt width, toward the leg opening 34.

The belt 40 may comprise a seventh force zone 122, a eight force zone 124, a ninth force zone 126, a tenth force zone 128, a eleventh force zone 130, and a twelfth force zone 132 located in the back belt 86. The seventh force zone 122, eight force zone 124, and ninth force zone 126 may be located in the third elastic section 106. The tenth force zone 128, eleventh force zone 130, and twelfth force zone 132 may be located in the fourth elastic section 108. The seventh force zone 122, eighth force zone 124, ninth force zone 126, tenth force zone 128, eleventh force zone 130 and twelfth force zone 132 may comprise a transverse force of 0 to 10N/zone. The seventh force zone 122 is adjacent to the leg opening 34. The twelfth force zone 132 is adjacent to the waist opening 36. The seventh force zone 122, eighth force zone 124, and at least part of the ninth force zone 126 are located within lower two third of the back belt width, toward the leg opening 34. Force zones may be equally distanced throughout the belt along the longitudinal axis in the front and back belts 84, 86. Force zones may also be unequally distanced throughout the belt along the longitudinal axis in the front and back belts 84, 86. Force zones may have varying width and length. Force zones may be continuous or discontinuous, as for example, when disrupted by the main body 38 and/or absorbent core.

The front belt 84 may comprise 5 to 50 elastic strands. The front belt 84 may comprise 10 to 20 elastic strands. The back belt 86 may comprise 5 to 50 elastic strands. The back belt 86 may comprise 10 to 20 elastic strands. The elastic strands are distributed amongst the different force zones. Elastic strands may be distributed evenly amongst the force zones. Elastic strands may also be distributed unevenly amongst the different force zones. Each force zone comprises at least one elastic strand.

The elastic strands may have a linear density between 200 to 2500. Linear density is the density of the elastic fibers in the elastic strand. The most commonly used unit for the linear density is the decitex, abbreviated dtex, which is the mass in grams per 10,000 meters. The linear density may be used to change the force profile. For example, one could reach a desired force profile by selecting the linear density of a single elastic strand, combining multiple elastic strands with a smaller linear density in close proximity to each other, and/or combining with other elastomeric materials.

The elastic strands may have an elastic pre-strain. The elastic pre-strain is the percent of length increase in an elastic strand or plurality of elastic strands at the point of combining the elastic(s) with the first and/or second belt layers. For example a strand with a free length of 15 centimeters (cm) may have a load applied such that the 15 cm elastic strand is now 18 cm long. This length increase of 3 cm is 20% of 15 cm (3/15), or a 20% strain. The elastic pre-strain may be used to change the force profile of a single elastic strand or a plurality of elastic strands. Force profiles may also be changed by changing the linear density in conjunction with the elastic pre-strain of one or more elastic strands.

The elastic pre-strain of the eighth force zone 124 found in the third elastic section 106 of the back belt 86 may be greater than, equal to, or less than the elastic pre-strain of both the seventh force zone 122 and the ninth force zone 126. The elastic pre-strain of the eleventh force zone 130 found in the fourth elastic section 108 of the back belt 86 may be greater than, equal to, or less than the elastic pre-strain of both the tenth force zone 128 and the twelfth force zone 132.

The linear density of the elastic in the eighth force zone 124 found in the third elastic section 106 of the back belt 86 may be greater than, equal to, or less than the linear density of the elastic in one or both of the seventh force zone 122 and the ninth force zone 126. The linear density of the elastic in the eleventh force zone 130 found in the fourth elastic section 108 of the back belt 86 may be greater than, equal to, or less than the linear density of the in one or both the tenth force zone 128 and the twelfth force zone 132.

The force of the first elastic section 102 may not be equal to the second elastic section 104. The force of the third elastic section 106 may not be equal to the fourth elastic section 108. Elastics located in the fourth elastic section 108 transversely cover substantially the whole section continuously. Elastics located in the third elastic section 106 may be laterally interrupted by the main body 38 and/or absorbent core.

The number of elastic strands in each zone may be changed according to the placement of the absorbent core. Applicants have found that the use of thinner absorbent cores may lead to a need in increased elastic force to compensate for the change in article thickness. The force profile must be adjusted depending on the location and thickness of the absorbent core. This particularly affects the second elastic section and third elastic section.

The elastic strands disposed in the belt may be aligned in a curved fashion so that the a tangent of the curve of the elastic strands may form an acute angle with the centerline or may form an arcuate shape. This may allow for targeting the force profile and/or coordinating print and elastication/rugosities/elastics in the stretch sections.

The eight force zone 124 of the third elastic section 106 contains a greater or equal force profile than the seventh 122 and ninth 126 force zones. The eleventh force zone 130 of the fourth elastic section 108 contains a greater or equal force profile than the tenth 128 and twelfth 132 force zones.

The gaps between the elastic strands may be 3 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, or 22 mm. The gap between elastic strands in the second force force zone 112 and the eleventh force zone 130 may be larger than the gap between elastic strands in the first 110 and third 114 force zones or the tenth 128 and twelfth 132 force zones, for example, 20 mm. The gap between the twelfth force zone 132 and the waist opening 36 may be between about 15 mm to 40 mm. The gaps also apply to the gaps between transversely extending elements of a scrim material matrix.

A spacer 136 between the first elastic section 102 and the second elastic section 104 may be at least 1.5, 2, 3, or 4 times greater than the average spacing of the elastics disposed in one or both of the elasticity sections. A spacer 136 between the third elastic section 106 and the fourth elastic section 108 may be at least 1.5, 2, 3, or 4 times greater than the average spacing of the elastics disposed in one or both of the other elasticity sections. A spacer 136 may also be between at least two alternating zones in the front belt portion 84 and the back belt portion 86. The spacer 136 may be least 1.5, 2, 3, or 4 times greater than the average spacing of the elastics disposed in one or both of the elasticity sections.

Applicants have surprisingly found that by changing the force profile throughout one or both of the front and back portions of the belt 84, 86 so that the second force zone 112, fifth force zone 118, eighth force zone 124, and eleventh force zone 130 have a greater force profile than the adjacent zones creates an improved fit and comfort of the absorbent article. The force profile described translates into an improved fit with reduced sagging and or gapping problems around the waist opening. The gap mentioned in the paragraph immediately above allows for the caregiver or user to easily apply and remove the absorbent article. This profile can similarly be represented by alternate high low force profile force zones. An increased force profile of the second force zone 112 also allows the caregiver or user to stretch the absorbent article with less force since the force profile of the first force zone 110 is less than that of the second force zone 112.

Test Methods Section
Test Equipment/Environment

A suitable tensile tester such as an MTS Alliance with MTS Testworks version 4.0 or equivalent instrument is used. The tester is equipped with flat clamps that are capable of holding at least the entire transverse length of the side seam should be used. The instrument is calibrated according to the manufacturer's specification. Testing is performed at 23° C.±2° C. and 50%±2% relative humidity.

Sample Prep

The side seams of the product are broken to separate the front belt from the back belt. The respective force zones (as described in the Detailed Description of the Invention) are cut away from these belts. Each separated section of the front and back belt will be referred to as a "test sample" herein. All material layers, including the chassis components, should be kept with the test sample. All cut lines are straight, parallel to the transverse direction of the absorbent article. Each test sample needs to have at least one elastomeric material. The widths (a dimension in the longitudinal direction of the absorbent article) of the respective zones are measured.

The length of the test sample is determined. The length measures in the transverse direction of the absorbent article a distance from one end to the other end of a test sample in a fully stretched condition. The fully stretched condition is the condition where the test sample is stretched by the force of 0.1 N/mm multiplied by the width of the test sample. If one or both ends of a test sample are not parallel to the longitudinal direction, the shortest length within the test sample is considered as the length of the test sample.

An adjusted test sample length is defined such that the length of a test sample minus the combined length of any material in the upper and lower clamps. Thus, if a test sample is mounted in the clamp so that 10 mm at each end is held in the clamps, then the adjusted belt length is the measured belt length minus 20 mm.

The test samples are kept unstretched at least for 10 min before the test.

Test

For each test sample, the initial gauge length of the tensile tester is set to allow the test sample to be mounted in a relaxed state. The load cell is zeroed to offset the sample weight.

The test sample is stretched in the transverse direction of the absorbent article at a rate of 254 mm/min, and a load (N) is measured within 5 sec after the test sample reaches at 65% of the adjusted test sample length. The transverse force is calculated for each of the force zones according to an equation:

A transverse force($N$/mm)of a test sample=Measured value($N$)/width of the force zone(mm)

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline, a transverse centerline, a front region, a crotch region, and a back region, the absorbent article comprising:
   a main chassis portion comprising an absorbent main body, and a waist portion; the waist portion comprising a belt portion; the belt portion comprising a front belt portion and a back belt portion; the main absorbent body comprising an absorbent core;
   wherein the front belt and the back belt portions are joined at side edges to form a first seam comprising a first end and a second end and a second seam comprising a first end and a second end;
   wherein the first ends of the first and second seams are disposed immediately adjacent to the waist opening, and wherein the second ends of the first and second seams are disposed immediately adjacent to the leg openings;
   wherein a transverse seam axis intersects each of the second ends of the first and second seams, and runs substantially parallel to the transverse centerline;
   wherein the front belt portion comprises a first elastic section comprising a first force profile and a second elastic section comprising a second force profile;

wherein the first elastic section comprises a first plurality of elastics comprising elastic strands having a first average spacing;

wherein the second elastic section comprises a second plurality of elastics comprising elastic strands having a second average spacing;

wherein the back belt portion comprises a third elastic section comprising a third force profile and a fourth elastic section comprising a fourth force profile;

wherein the third elastic section comprises a third plurality of elastics comprising elastic strands having a third average spacing;

wherein the fourth elastic section comprises a fourth plurality of elastics comprising elastic strands having a fourth average spacing;

wherein the front belt comprises a spacer;

wherein a surface of the front belt portion and a surface of the back belt portion is formed from a first belt layer extending from a first waist edge in a first waist region through the crotch region to a longitudinally opposing second waist edge in a second waist region and forms at least a portion of an outer surface of the absorbent article;

wherein the surface extending from a first waist edge to a longitudinally opposing second waist edge folds at the front waist edge forming a portion of the of an inner surface of the front waist belt;

wherein the distance between the absorbent main body and at least one of the back waist edge or the front waist edge is greater than the distance between the absorbent main body and the back waist edge or the front waist edge;

wherein the at least a portion of the third plurality of elastics of the back belt overlap the at least a portion of the absorbent core;

wherein each of the first plurality of elastics in the first elastic section are parallel to the transverse centerline;

wherein each of the plurality of second elastics in the second elastic section are parallel to the transverse centerline;

wherein at least a portion of the second plurality of elastics of the second elastic section or a portion of the third plurality of elastics of the third elastic section are disposed between the transverse seam axis and the transverse centerline;

wherein the spacer is at least 1.5 times greater than an average spacing of the first average spacing of the first plurality of elastics;

wherein the absorbent article comprises a leg elastic material extending along a side edge of the absorbent main chassis; and wherein a portion of the second plurality of elastics in the second section are along a leg cutout.

2. The absorbent article of claim 1, wherein the spacer is at least 1.5 times greater than an average spacing of the first average spacing of the first plurality of elastics or the second average spacing of the second plurality of elastics.

3. The absorbent article of claim 1, wherein the elastic strands exhibit a linear density and a force prestrain.

4. The absorbent article of claim 3, wherein the front belt force profile is achieved by changing the linear density of the elastic strands.

5. The absorbent article of claim 1, wherein the first elastic section force profile is different than the second elastic section force profile.

6. The absorbent article of claim 1, wherein the first elastic section of the front belt portion comprises a first force zone, a second force zone, and a third force zone;

wherein the second elastic section of the front belt portion comprises a fourth force zone, fifth force zone, and a sixth force zone;

wherein the individual force zones each comprise an individual force profile; and wherein the force profile of the first zone, second zone, or third zone does not equal the force profile of the fourth zone, fifth zone, or sixth zone.

7. The absorbent article of claim 1, wherein main chassis has a generally rectangular shape.

8. The absorbent article of claim 1, wherein the front belt and the back belt refastenably connect at one or both of the first seam and the second seam.

9. The absorbent article of claim 1, wherein the front belt and the back belt refastenably connect to the absorbent main body.

10. The absorbent article of claim 1, wherein the spacer is between the first elastic section and the second elastic section.

11. The absorbent article of claim 1, wherein the absorbent core comprises a fluid acquisition component, a fluid distribution component, and a fluid storage component.

12. The absorbent article of claim 1, wherein the first average spacing is greater than at least one of the second average spacing, the third average spacing, or the fourth average spacing.

* * * * *